US 6,706,015 B2

(12) United States Patent
Bang

(10) Patent No.: US 6,706,015 B2
(45) Date of Patent: Mar. 16, 2004

(54) SAFETY SYRINGE

(75) Inventor: Young Chul Bang, Seoul (KR)

(73) Assignee: Medexel Korea, Los Angeles, CA (US)

( * ) Notice: Subject to any disclaimer, the term of this patent is extended or adjusted under 35 U.S.C. 154(b) by 87 days.

(21) Appl. No.: 10/142,577

(22) Filed: May 7, 2002

(65) Prior Publication Data

US 2003/0212366 A1 Nov. 13, 2003

Related U.S. Application Data

(63) Continuation-in-part of application No. 10/048,199, filed on Jan. 25, 2002, which is a continuation-in-part of application No. 09/550,504, filed on Apr. 14, 2000.

(51) Int. Cl.$^7$ ............................................... A61M 5/00
(52) U.S. Cl. ....................................... 604/110; 604/195
(58) Field of Search ................................. 604/110, 181, 604/182, 186, 187, 218, 191–198, 221, 222, 228, 238, 240, 263, 264, 272; 128/919; 206/364, 571

(56) References Cited

U.S. PATENT DOCUMENTS 5,205,824 A * 4/1993 Mazur ........................ 604/110
5,256,151 A * 10/1993 Chul ........................... 64/195
5,533,970 A * 7/1996 Berger et al. ............... 604/110

FOREIGN PATENT DOCUMENTS

EP          0704225 A2 *   3/1996

* cited by examiner

Primary Examiner—Brian L. Casler
Assistant Examiner—Michael M Thompson
(74) Attorney, Agent, or Firm—Cislo & Thomas LLP

(57) ABSTRACT

The invention provides a safety syringe, which has a cylinder (11), a syringe needle (21), a needle holder (31) associated to the cylinder and adapted to hold the syringe needle, and a plunger (41) associated to the cylinder (11), wherein the plunger (41) comprises a piston (42) and serves to inject a filling of the cylinder (11) via the syringe needle (21), and wherein the plunger (41) can be coupled with the needle holder (31) arranged in the region of a front hole (12) of the cylinder (11), to retract the needle holder (31) together with syringe needle (21) into the cylinder (11) by pulling the plunger (41) once coupled to the needle holder (31) is retracted into the cylinder by rotating the plunger (41) and pulling the plunger (41) aft thereby pulling the needle holder (31) into the cylinder (11). Then the aft end of the plunger (41) is broken off, and a removable cap (49) from the aft end of the plunger (41) may be placed over the opening in the forward end of the cylinder (11).

8 Claims, 14 Drawing Sheets

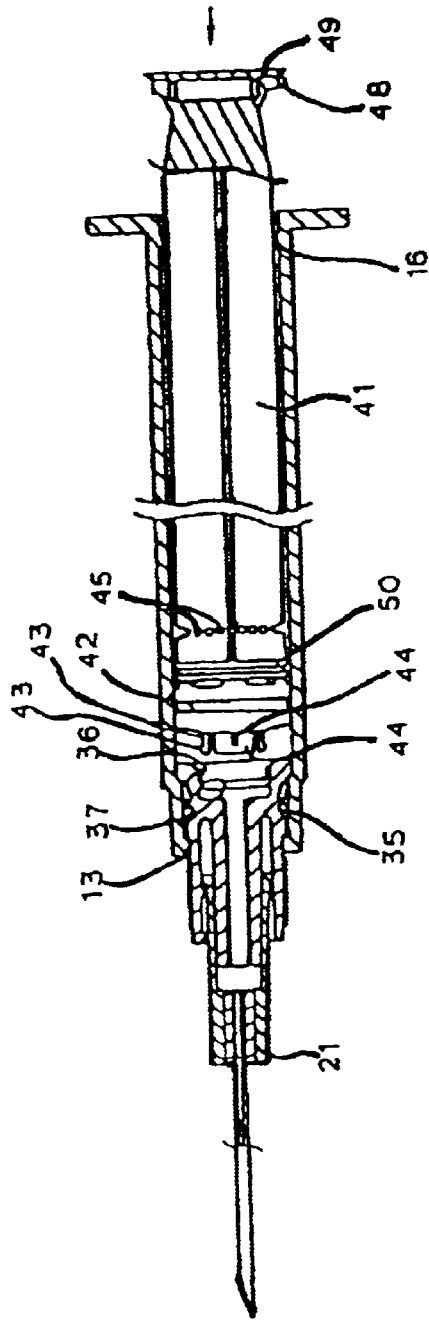
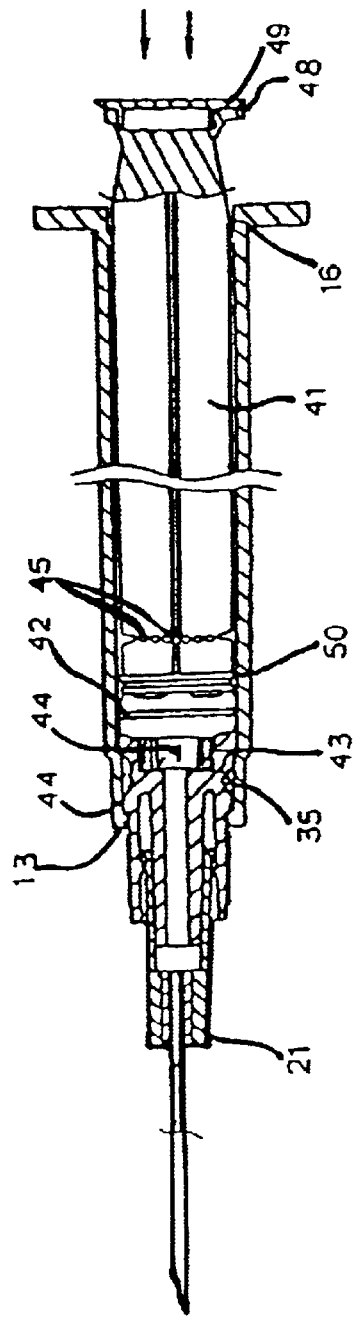
Fig. 9
Fig. 10

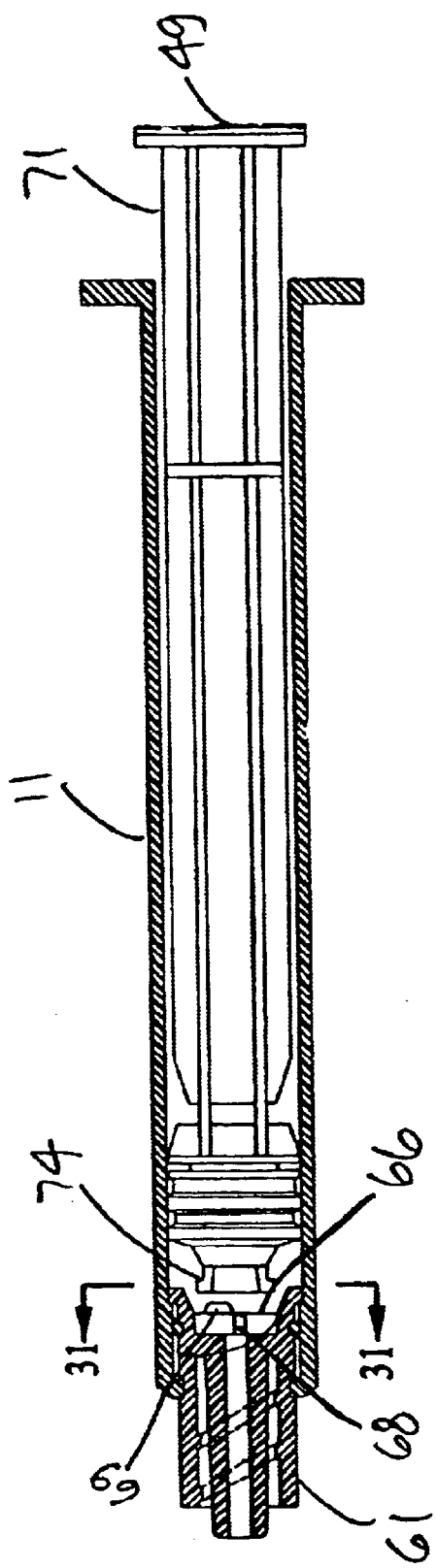
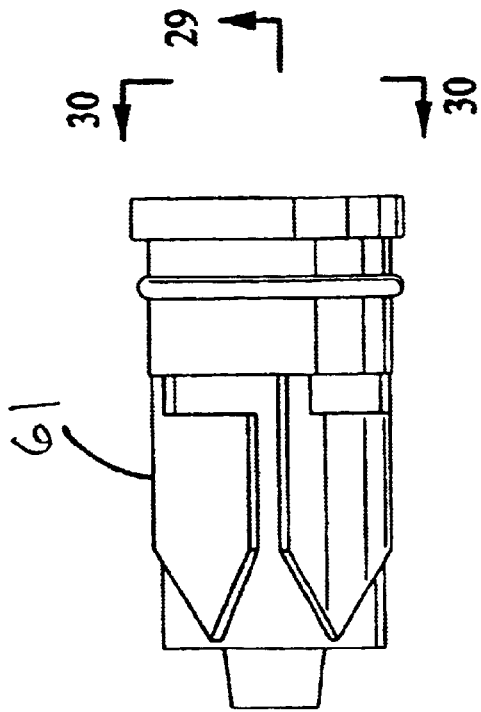
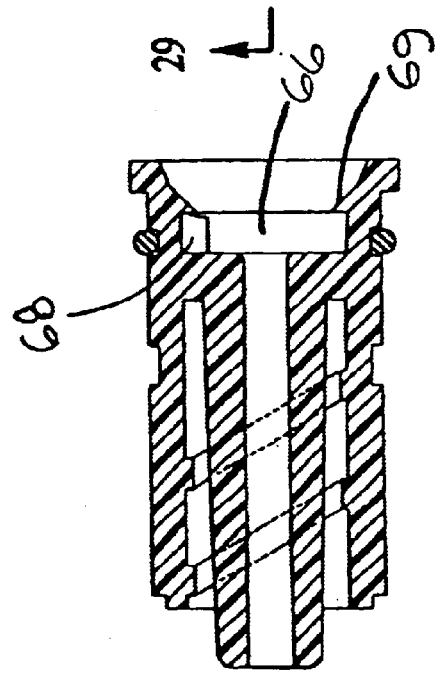
Fig. 27
Fig. 28
Fig. 29

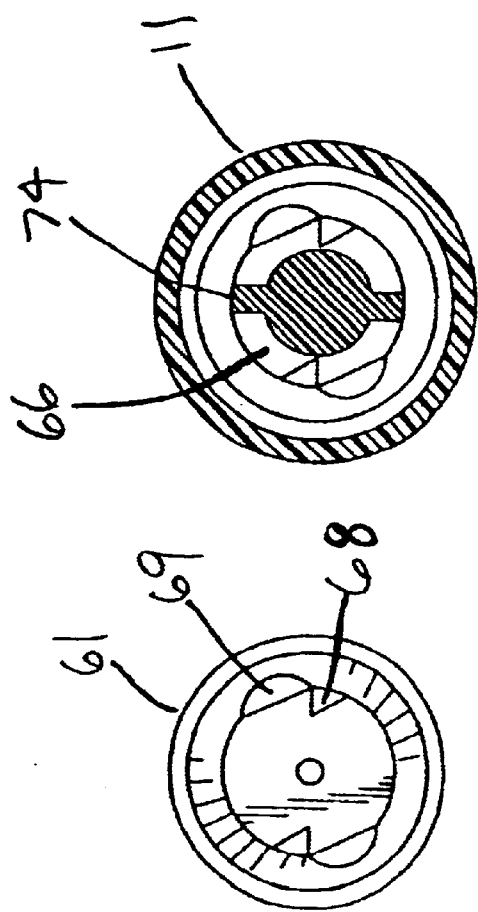
Fig. 31
Fig. 30
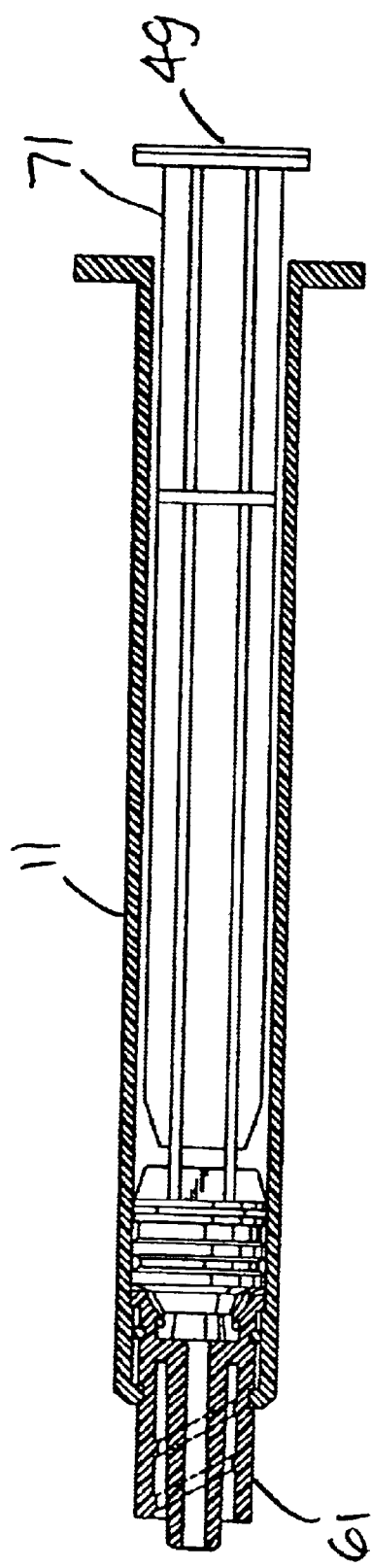
Fig. 32

SAFETY SYRINGE

CROSS-REFERENCES TO RELATED APPLICATIONS

This patent application is a continuation-in-part of application Ser. No. 10/048,199 filed Jan. 25, 2002, which is a continuation-in-part of application Ser. No. 09/550,504 filed Apr. 14, 2000.

BACKGROUND OF THE INVENTION

1. Field of the Invention

This invention relates generally to hypodermic syringes, and more particularly to such syringes having retractable needles after use to prevent hazardous needle sticks.

2. Description of the Related Art

The idea of safety syringes with retractable needles to prevent needle sticks is well known. Initially such devices were bulky, expensive to manufacture and did not function well. Over the years as the art progressed they became easier to make and operate, but still problems remain which have prevented mass manufacture and use of safety syringes.

Disposable syringes are typically made by automated, high volume plastic injection molding processes. Since these devices by design are disposable after one use, they must be very inexpensive to produce on a per unit basis. The critical parts of the syringe must be structurally sound and well made. Given the uses of syringes in administering drugs, stringent quality standards must be maintained.

Mazur U.S. Pat. No. 5,401,246 disclosed a retractable syringe with a needle holder and needle in a frangible connection in the forward end of a syringe barrel. This syringe includes an additional part, a clip at the forward end of the barrel, which locks the needle holder in place and prevents inadvertent release from the forward end of the barrel. To release the needle holder the user must manually manipulate the clip near the needle, to unlock the needle holder and allow its retraction into the barrel. This manipulation near the needle is believed fraught with danger. As is common, the plunger may be broken off at a weakened section and reinserted into the other end of the barrel. This device is also believed unnecessarily complex.

Gloyer U.S. Pat. No. 5,304,154 disclosed a retractable syringe with a needle holder in an articulating connection with a thin walled barrel. Protrusions in the needle holder and slots in the barrel together provide a mechanism for retaining and releasing the needle holder. This patent further discloses a plunger/needle holder single-use snap connection consisting of a protruding latch in the plunger and a corresponding cavity in the needle holder. Given the variations in wall thickness of the barrel section to provide the slots, and the complicated geometry of the needle holder cavity for the snap connection, this device is believed difficult and expensive to manufacture, and subject to quality problems.

SUMMARY OF THE INVENTION

A safety syringe for injecting or withdrawing fluids and avoiding inadvertent needle sticks after use includes a thin-walled cylinder or barrel fillable with the fluids, a generally cylindrically-shaped needle holder that slides inside the barrel, and a hollow needle attached to the forward end of the needle holder. The needle holder has a through passageway near its central axis, such that the needle and barrel are in fluid communication. The outer surface of the needle holder has a number of L-shaped grooves, and the forward end of the inner surface of the cylinder has a number of corresponding protrusions sized to be received by the L-shaped grooves, to releasably secure the needle holder to the forward end of the barrel.

The aft end of the needle holder has a generally cylindrically-shaped cavity with a number of upstanding webs or stops. The plunger at the forward end has a piston slidably engaged with the inner surface of the barrel, the piston having a rod extending to the aft end of the plunger. The forward end of the plunger further has an anchor while the aft end of the needle holder has a corresponding generally circular opening and latch sized to receive and retain the anchor inside the cavity of the needle holder upon insertion thereon and rotation of the plunger. The anchor has a plurality of flukes sized to catch on the stops or upstanding webs in the needle holder cavity as the plunger is rotated about its central axis; positioning the anchor to be engaged by the latch. Preferably, the latch is merely a portion of the opening of reduced diameter. The forward end of the piston rod may have a reduced cross section, preferably a notch, to facilitate breaking off of the plunger.

After use of the safety syringe the plunger anchor may be pushed inside the needle holder cavity and the plunger rotated about its central axis. Advantageously, if somehow inadvertently coupled together, the needle holder and plunger may be decoupled by rotating the plunger back the other direction and pulling the plunger anchor outside the needle holder cavity. Instead, going forward with retracting the needle, the plunger is further rotated and pulled back, moving the needle and holder inside the barrel. Then the plunger broken off at its reduced cross section, effectively disabling the safety syringe from further use. Optionally a removable cap may be taken from the aft end of the plunger and inserted into the open forward end of the barrel.

Preferably there is an O ring on the outer surface of the needle holder for sealing any gap between the needle holder and the inner surface of the barrel. Preferably there is another O ring on the outer surface of the piston for sealing any gap between the outer surface of the piston and the inner surface of the barrel.

Preferably the L-shaped slots have widened V-shaped entrances, for ease of receiving the protrusions in assembling the safety syringe. Preferably the protrusions are at the forward edge of the inner surface of the thin walled barrel, for ease of manufacture. Preferably the thin-walled barrel is a substantially constant diameter and thickness except for the plurality of protrusions.

OBJECTS OF THE INVENTION

Given the shortcomings of the prior art, further significant improvements to safety syringes are desirable.

It is an object of the present invention to provide a safety syringe that minimizes the possibility of inadvertent needle sticks;

It is an object of the present invention to provide a safety syringe that prevents reuse of the syringe after one use;

It is an object of the present invention to provide a safety syringe that is inexpensive to manufacture;

It is an object of the present invention to provide a safety syringe that is easy to make without quality problems;

It is a further object of the present invention to provide a safety syringe that is simple to use;

It is a further object of the present invention to provide a safety syringe with a cap to seal the barrel once the needle is retracted therein.

It is a further object to provide a safety syringe in which if the plunger and needle holder are inadvertently coupled together they may be easily separated.

These and other objects and advantages of the present invention will be apparent from a review of the following specification and accompanying drawings.

BRIEF DESCRIPTION OF THE DRAWINGS

FIG. 9 is a cross-sectional view of this device when injection is completed.

FIG. 10 is a cross-sectional view of the device when plunger meets the syringe needle fixer upon completion of injection.

FIG. 27 is a section view illustrating the needle holder and cylinder and a side view of the plunger of the third embodiment;

FIG. 28 is an orientation view illustrating the needle holder and the various views taken from and through it;

FIG. 29 is a section view illustrating the needle holder;

FIG. 30 is a rear view illustrating the needle holder;

FIG. 31 is a section view of the plunger and cylinder; and

FIG. 32 is a side view illustrating the plunger engaging the needle holder.

DESCRIPTION OF THE PREFERRED EMBODIMENT(S)

Figure 1:
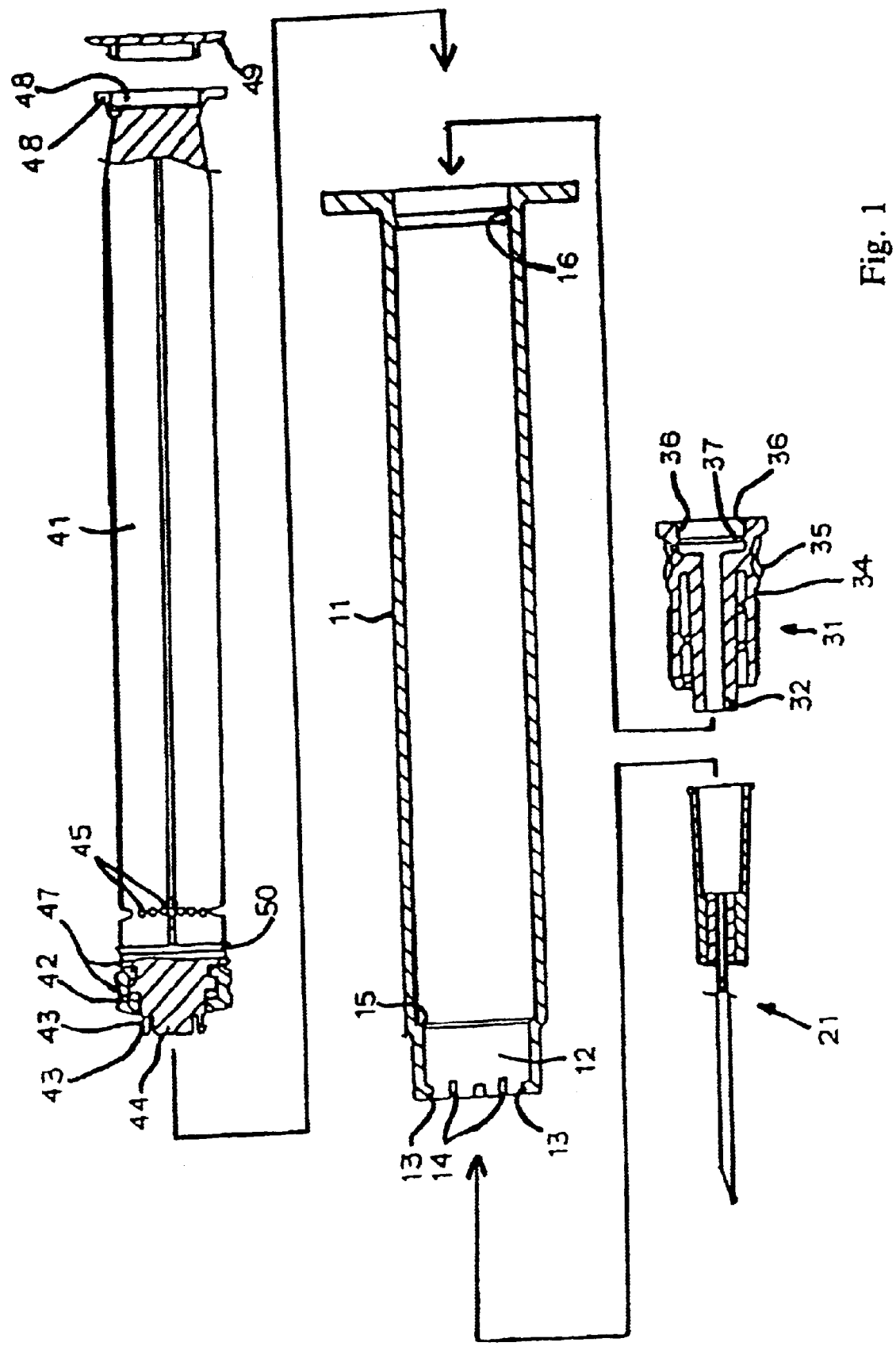
FIG. 1 is cross-sectional view of the parts.
Figure 2:
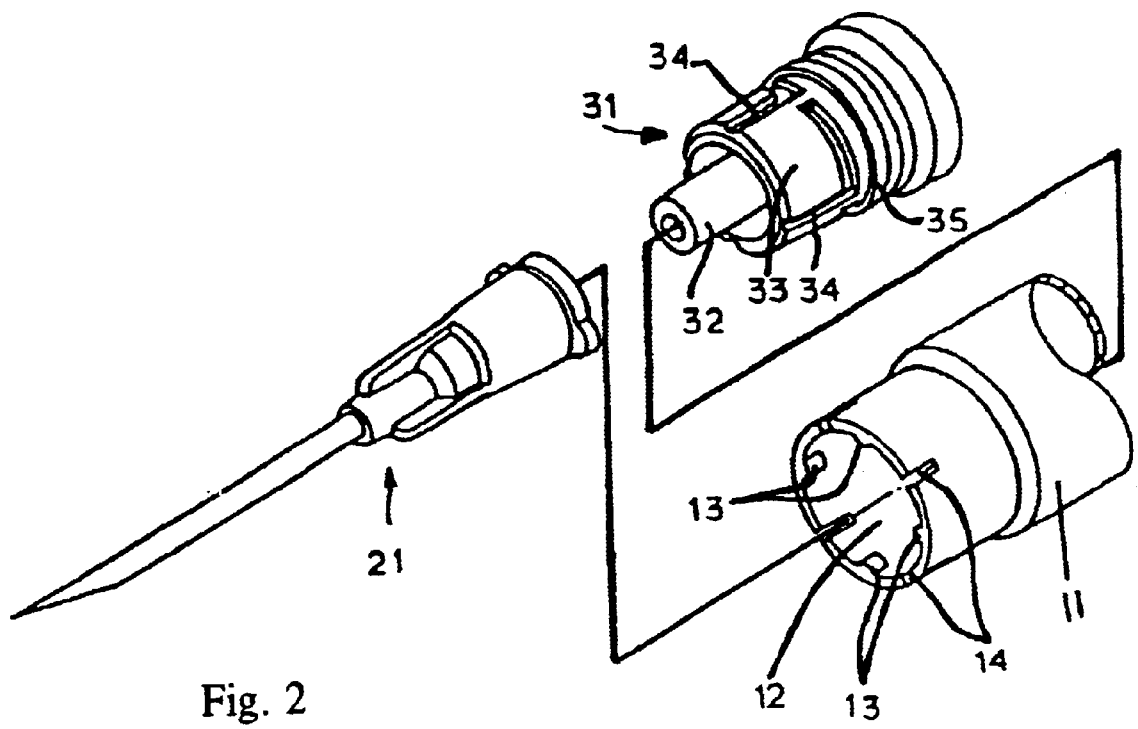
FIG. 2 is a squint view of the parts.
Figure 3:
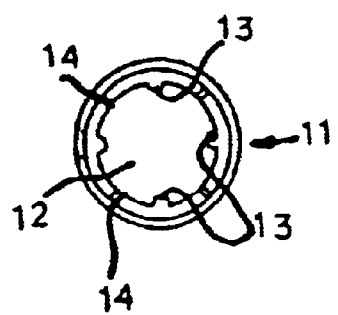
FIG. 3 is a lateral view of the cylinder.
Figure 4:
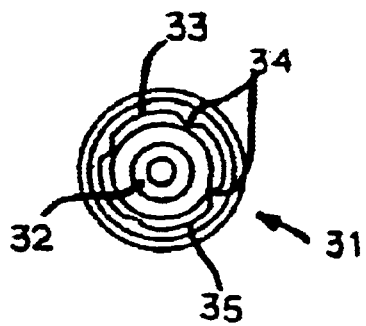
FIG. 4 is a lateral view of the syringe needle inserter.
Figure 5:
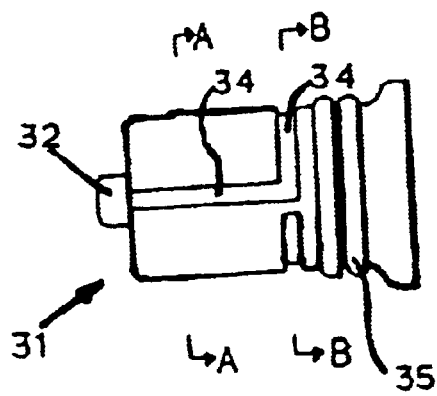
FIG. 5 is a front view of the syringe needle inserter.
Figure 6:
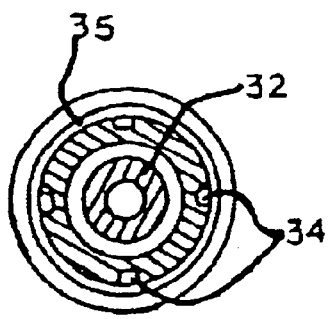
FIG. 6 is an A—A line cross-sectional view of the FIG. 5.
Figure 7:
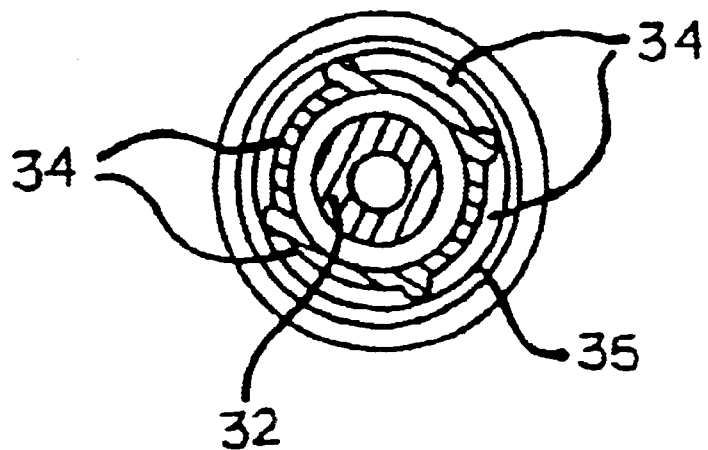
FIG. 7 is a B—B line cross-sectional view of the FIG. 5.
Figure 8:
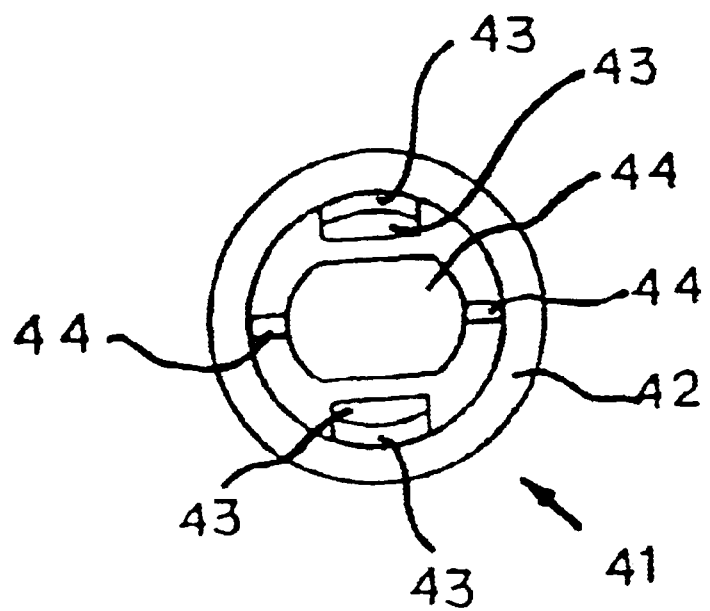
FIG. 8 is a front view of the plunger.

The detailed description set forth below in connection with the appended drawings is intended as a description of presently preferred embodiments of the invention and is not intended to represent the only forms in which the present invention may be constructed and/or utilized. The description sets forth the structure and the sequence of steps for constructing and operating the invention in connection with the illustrated embodiments. It is to be understood, however, that the same or equivalent structure and sequences of steps may be accomplished by different embodiments that are also intended to be encompassed within the spirit and scope of the invention.

This device is for a safety syringe preventing a third person from getting damaged by the used syringe needles. It is designed to keep the syringe needle in custody of syringe cylinder once used so that a third person may not be pricked by the used needles. The plunger shall then be broken after use in order to prevent from being used again.

In order to prevent repeated use of syringe needles by far, it is the current phenomenon that disposable syringes are predominantly being used. Such conventional disposable syringes have been technically designed to prevent to be reused.

The conventional disposable syringes are, however, after being used, usually or frequently being disposed or not properly dealt with the needles and thus a third person may be easily pricked. Such problems of giving damages to a third party have not been solved.

Because the syringe needles always have blood stains, in case medical workers including doctors and nurses as well as a third party get pricked by a used syringe needle they are very much concerned of being infected by the disease of the patients (AIDS, hepatitis, etc.) and such cases have been reported.

This device is a safety syringe system which prevents disease from being infected to a third party via used syringe needles by keeping it inside the syringe cylinder.

According to this device, the used needle does not need to be taken off from the syringe after use, but, instead, it is pulled into the cylinder to be fixed and kept in custody inside cylinder. And by doing this, infections of disease to a third party by getting pricked can be prevented.

My previous patent application of this nature regarding safety syringe system have been published on the Utility Model Announcement Korea Utility Model No. 91-4532 and Open Utility Model Public News Korea Utility Model No. 96-13409.

This device is to introduce more advanced safety syringe system which is simpler in structure and more reliable in affect compared with the above-said previous patent.

Technical Target that this device pursue to accomplish.

My previous safety syringe system published on the Utility Model Announcement No. 91-4532 and Open Utility Model Public News No. 96-13409 was to have the needleset fixed to the plunger so that the syringe needle can be kept inside cylinder when the plunger is pulled back.

This disposable syringe that I have patented as above had some defects requiring a host of parts and extreme preciseness whereby creating difficulties in manufacturing. This device has been developed instead. It is simpler in structure, easier in manufacturing, has eliminated the possibility of mis-use and requires less number of parts.

The following refers to FIGS. 1–11.

The safety syringe of the present invention has a cylinder for injection. Inside the cylinder are piston and plunger. In a syringe which the dead-end of the cylinder has a syringe needle usually affixed, cylinder (11), syringe needle (21), syringe needle inserter (31) and plunger (41) are the parts in structure. At the end of inserting of the cylinder are a host of projection (13) and incised grooves (14) arranged alternately. On the inner face of the cylinder are stopping sill (15) and obstacle (hooking) sill (16) at the rear end. At the center of the syringe needle inserter (31) is the syringe needle fixer (32). On the outer face (33) of barrel shaped syringe needle fixer (32) are number of "L" shaped grooves (34) for projections (13) to enter. Packing (35) is placed in its rear. Inside of the rear-end are projections prominence (36) on the top and bottom. Inside both of the up/down projections aforesaid is formed the obstacle (hooking) ring sill (37). On the tip of the plunger (41) where piston (42) is inserted are top/bottom connecting device (43) which have hooking sills (43'). On the both ends of the central projection (44) are erected projections (44'). At the end of the plunger (41) where piston (42) is inserted forms a space (47). Pressing button (48) at the rear part of the plunger (41) has a inserting groove (48'). The inserting groove (48') is for the cap (49) to be inserted to cover the inserting hole (12) of the cylinder tip.

In order for the plunger (41) to be easily broken at cutting notch (45), in the fore part of the plunger (41) are many "V" shaped grooves or holes and at the rear part of the piston (42) of plunger (41) is formed a stopping ring sill (50).

This device with such structure will act as follows:

Cylinder (11) and the syringe needle inserter (31) are combined together by thrusting the needle inserter (31) from the rear end of the cylinder (11) to the inside of the cylinder until the projections (13) on the inner face of the cylinder (11) insert hole (12) meet and set in the "V" shaped grooves formed on the outer face of the barrel shaped needle inserter (31).

Then the piston (42) inserted plunger (41) is pushed into the rear side of the cylinder (11). Right before the use of the syringe, syringe needle (21) is fixed in the syringe needle inserter (31) as usual. Injection is sucked into the cylinder (11) by pulling the plunger backward. Injection is done to the patient by pushing the plunger (41).

At the time when the syringe needle inserter (31) is fixed to the cylinder (11) from the rear toward inner side, it has to be pushed until the projections (13) of inserting hole (12) of the cylinder set in toward the circumference direction of the "L" shaped grooves of the syringe needle inserter (31). At this time, the incised grooves between projections (13) will help syringe needle inserter (31) entering into the cylinder (11) by making the cylinder (11) tip burst open so that the needle inserter (31) can be easily set in.

The stopping sill (15) of the inner face of the cylinder (11) joints the rear tip of the syringe needle inserter (31). The packing (35) inserted in the syringe needle inserter (31) will closely adhere to the inner face of the cylinder (11).

When the syringe inserter (31) is inserted by force into the inserting hole (12) of the cylinder (11) tip in order to fix the syringe needle inserter (31) onto the cylinder's (11) tip, the projections (13) of the inner face of the cylinder (11) will be hooked on any of the "L" shaped grooves (34) of the outer face of the syringe needle inserter (31), that is, on the groove of any location in circumference direction, but as the syringe needle inserter (31) turns accordingly when we turn and fix the syringe needle (21) in the syringe needle inserter (31), the projections (13) erected in the inserting hole (12) of the cylinder (11) will become to locate at the last of the "L" shaped grooves as soon as the syringe needle is fixed in.

Moreover, as the meeting places of the "L" shaped grooves are not flat but are "U" or "V" shaped, the projections (13) of cylinder (11) cannot be located on the border between the "L" shapes.

Like this, the syringe needle inserter (31) and syringe needle are fixed at the cylinder (11) tip, and by thrusting the plunger (41) into the cylinder (11), syringe assembly is completed. The syringe sucks the injection into the cylinder (11) when the plunger (41) is pulled back. After plucking the needle (21) from the patient (Ref. FIG. 9) upon completion of injection, if we apply force to push the plunger (41) (Ref. FIG. 10), piston (42) is being pressed so as for its volume to become smaller by the space (47) formed inside of the piston (42), and at the same time, the respective hooking sills (43') of upper and lower connecting device (43) formed up and down the plunger (41) is inserted in the obstacle ring sill (37) of the inner face of the rear part syringe needle inserter (31), plunger (41) tip and the syringe needle inserter (31) rear part will be combined together. When the plunger (41) is turned, the projection (44') erected both sides of the central projection (44) of the plunger tip will joint the up/down projections (36) of the rear inner face of the syringe needle inserter (31), and the turning plunger (41) will turn the syringe needle inserter (31).

The syringe needle inserter (31) which is turned by the plunger (41) is again turning the "L" shaped grooves (34), then the projections (13) of the cylinder (11) will turn the straight line of the "L" shaped grooves (34). When the plunger is drawn back, the projections (31) will be pushed forward along the straight lines of "L" shaped grooves, and at the same time, the needle inserter (31) as well as the syringe needle (21) which is inserted thereto will be pushed back to inside of cylinder (11).

Backtracking plunger (41) will retreat until the plunger ring sill (40) reaches the hooking sill (16), then plunger (41) is to be broken. Then all the operation comes to an end by trans-inserting the cap (49) which is inserted in the pressing hole (48) into the inserting hole (12) in front of the cylinder (11).

In the cap's (49) inserting hold is prepared a ring (circular) sill and because the ring sill of the cap (49) insert hole is to meet the projection (13) of the insert hole (12) of cylinder (11), the cap inserted in the insert hole (12) would not easily come out.

This device is designed to withhold the used syringe needle inside the cylinder, the main body of syringe, and whereby to prevent the possible damages which may happen to medical workers including doctors and nurses as well as a third party from being pricked by the used syringe needles.

The syringe needs to be dealt with utmost care regardless before or after use, due to the sharp-pointed needles. A special attention is required to be paid to the used ones because of the bloodstain. Especially, because hepatitis and AIDS are infectious to a third party via blood stain, the syringes used for patients of such disease must be handled with special attention.

However, as described in this device, if we insert the used syringe needle into the cylinder and then break the plunger, the syringe needle will be located inside the cylinder. If we cover the cylinder with the cap prepared in the rear of the plunger, there is no possibility at all for the syringe needle inside the cylinder to be exposed out of the cylinder and can be kept safely in custody until further process.

If we use this device, we cannot re-use the used syringes. Therefore, it is very useful device as it can prevent disease caused by the used syringe needles from being infectious to a third person.

This device is designed to keep the used syringe needle inside the cylinder prohibiting re-use of the used syringe needles in order to prevent possible damages for medical workers including doctors and nurses and a third party alike to be taken from being pricked by the used syringe needles. The syringe needle, which is fixed in the syringe needle fixer, is set at the tip of cylinder with the help of the syringe needle inserter.

Inserting part is composed at the projection of the tip of the plunger, which is to be put in the cylinder. At the rear end of the syringe needle fixer is formed the assembling part. The projection of the plunger joints the syringe needle fixer. When plunger is drawn back, syringe needle fixer with its needle fixed in will also be drawn back and kept inside the cylinder. Thus, damages by the used syringe needle can be prevented. This device is of the safety syringe which can prevent infectious diseases such as hepatitis and AIDS.

Some important aspects of the safety syringes according to the first embodiment are as follows:

It has a cylinder to suck in injection. Piston and plunger are in the cylinder while the ordinary syringe has the syringe needle affixed to the syringe, this device has the cylinder (11), syringe needle (21), syringe needle inserter (31) and plunger respectively as parts of its structure. At the insert hole (16) of the above said cylinder (11) tip are a host of projections (13) and incised grooves (14) arranged alternatively one after another. Cylinder's (11) inner face has stopping sill and hooking sill in the rear. At the center of the syringe needle inserter is a syringe needle fixer to fix syringe needle. Outer barrel shaped outer face of the syringe needle fixer has a number of "L" shaped grooves for projections (13) formed on the inner face of the insert hole (12) to set in. Packing (35) is set in the rear. On the upper and lower part of the inner face of the rear part are projections (36). Inside the upper and lower projections (16) is hooking ring sill (37). At the plunger (41) tip where piston is inserted are top and bottom joints connecting device which has hooking sill (43'). On both sides of the central projection (44) inside the top/bottom joint connecting device. Space (47) is formed at the plunger (41) tip where piston is inserted in. At the pressing/pushing button (48) of the rear end of the plunger (41) has the insert groove (48'). In the insert groove (48'), a cap (49) is supposed to be inserted to cover insert hole (12) of the cylinder tip.

In the following, a safety syringe according to the second aspect and further aspects of the invention is explained.

This device relates to a safety syringe so as to prevent the pricking of another person by means of withdrawing a needle in the inside of a barrel keeping in it after injection and the reuse of a syringe by means of breaking off a plunger.

The prior single use syringe which a technical method is applied to in order to prevent the reuse of a used syringe was usual.

But there was the possibility of pricking by a used needle because the prior single use syringe is left or thrown away, holding the needle on the syringe. Thus the problem that another person might be damaged with the used needle could not be solved by the single use syringe.

That is, some blood is left on the needle after injection. In that case, if doctor, nurse, medical employee or other person was pricked by the used needle, they might be infected with the disease of the patient (such as AIDS, hepatitis and the like) by it. The examples are actually reported.

This device relates to the safety syringe so as to prevent transmitting the infectious diseases through the used needle, withdrawing the used needle into the inside of a barrel and keeping it in a barrel without removal of the needle, after injection.

As prior patent documents on a safety syringe, there is Utility Model Announcement #91-4532 and Open Utility Model Announcement #96-13409 which were applied by this applicant and were announced. And also this applicant applied for utility model of a safety single use syringe in Utility Model Application #7783 in 1999.

This device has more simple structure and exact function than prior syringes which was applied by this applicant before.

The safety syringes that the needle set is fixed to the plunger, withdrawn into the inside of a barrel and kept in it after injection are shown in Utility Model Announcement #91-4532, Open Utility Model #96-13409 and Utility Model Application #7783, which were applied by this applicant and announced.

The prior single use syringes which were applied for utility model by this applicant had a problem in manufacturing because those need a great number of parts and high precision as this device is newly developed in order to remove the demerits, it needs few number of parts, the structure is simple, manufacturing is easy and the possibility of the incorrect operation gets removed.

In the following it is referred to FIGS. 12 to 25.

Structure of Device

Same as general syringe has a barrel which medication is sucked into, a piston and a plunger in the inside of a barrel.

This safety single use syringe is composed of a barrel (11), a needle (21), a plunger (41) and a needle inserting device (31) to which a needle (21) is attached. A number of projections (13) are in the inside of the front end of an inserting hole (12) of the above barrel (11), an annular restraining prominence (16) is at the rear end of a barrel, a needle locking device (32) to attaché a needle (21) is at the center of a needle inserting device (31), a number of "L" shaped female grooves (34) having the wide entrances in order to be assembled with a projection (13) located at an inner surface of an inserting hole (12) of the above cylindrical barrel (11) are on the outer cylindrical surface (33) of a needle locking device (32), an O-ring (35) is inserted at the rear of the grooves, a number of female grooves (37) are in the inside of a needle inserting device (31), a male extensions (43) having each restraining prominence (43') are at the front end of a plunger (41) to be assembled with a piston (42), an empty space (47) is at the front end of a plunger (41) to be assembled with a piston (42), a cutting notch (45) is at the front part of a plunger (41) in order to be easily broken off, an annular stop prominence (50) is at the rear part of a plunger (41), rear stop projections (51) are at the longitudinal center of a plunger, an empty space (53) is longitudinally in the central inside of a plunger (41) between rear stop projections (51) and cutting notch.

The device having this structure operates as follows:

A needle inserting device (31) is inserted into a barrel from the back end of a barrel (11) and pushed towards the front end until a number of projections (18) in the inside of an inserting hold (12) of a barrel (11) reaches the end of "L" shaped groove (34) having a wide entrance on the cylindrical outer surface (33) of a needle inserting device (31), and assembled with a barrel (11).

And then a plunger (41) assembled with a piston (42) is inserted into a barrel from the back end of a barrel (11) and a needle (21) is put into a needle inserting device (31) just before using a syringe. A plunger (41) is pulled back and medication is sucked into the inside of a barrel (11) as usual. Medication is injected into a patient's body, a plunger (41) being pushed.

When a needle inserting device (31) is inserted into a barrel (110) from the back end of a barrel (11) and fixed to a barrel, a needle inserting device (31) is pushed into a barrel until a number of projections (13) in the inside of an inserting hole (12) of a barrel (11) reaches the end of the "L" shaped groove (34) having the wide entrance on the outer surface of needle inserting device (31). In this case an annular stop prominence (15) on the inner surface of a barrel (11) meets the back end of a needle inserting device (31) and an O-ring (35) inserted into a needle inserting device (31) clings to the inner cylindrical surface of a barrel (11) so that sealing is completely kept.

When a needle inserting device (31) is pushed into an inserting hole (12) at the front end of a barrel (11) and locked, the projections (13) on the inner circumferential surface of a barrel (11) is positioned at the back end (the entrance of the groove) of the "L" shaped female groove (34) having the wide entrance on the outer circumferential surface of a needle inserting device (31). But when a needle (21) is put into a needle inserting device (31) and locked, the male projections (13) in the inside of an inserting hole (12) of a barrel (11) is positioned at the end of "L" shaped female groove (34) because both the needle (21) and the needle inserting device (31) are rotated together.

Thus, a needle inserting device (31) and a needle (21) is at the front end of a barrel (11) and a plunger (41) is inserted into a barrel (11) so that the assembly of a syringe is finished. The plunger (41) is pulled back, the medication is sucked into a barrel and it is injected to a patient's body, after medication is injected to a body and a needle (21) is withdrawn from it, as additional force is applied to a plunger (41) (FIG. 5), a piston (42) which has an empty space (47) inside is pressed and squeezed. At the same time each restraining stop projections (43') of a locking device (43) is locked in the inside of a female groove (37) located at the outside of a central hole of a needle inserting device (31) so that the front end of a plunger (41) is connected with the back end of a needle inserting device (31). Thereafter, if a plunger is rotated, a needle inserting device (31) is rotated together by it.

Thus a "L" shaped female groove (34) on the outer surface of a needle inserting device (31) rotated by a plunger (41) is rotated together so that projections (13) on the inner circumferential surface of the front end of a barrel (11), which are positioned circumferentially in a "L" shaped female groove (34), are rotated until the straight line of a "L" shaped female grove (34), after that, when a plunger (41) is pulled back, projections (13) is moved forward through the straight line of a "L" shaped female groove (34), and simultaneously a needle inserting device (31) with an attached needle (21) is moved back into a barrel (11) and kept inside.

A plunger (41) is moved backwards until a plunger annular prominence (50) reaches a restraining annular prominence (16) of a barrel (11). And then, a plunger is broken off at a cutting notch (45). Thus the broken plunger (42) is inserted into a barrel from the front end of a barrel. In other words, a rear restraining stop projection (51) of a plunger (41) is inserted until it reaches the inside of a projection (31) located in the inside of a front inserting hole (12) of a barrel (11). A plunger (41) which is locked in an inserting hole (12) is not pulled back easily because a rear restraining stop projection (51) is engaged with a projection (31) in the front end of an inserting hole.

Consequently, a needle inserting device (31) including a needle (21) is thoroughly inserted into the inside of a barrel (11). A needle stored in the inside of a barrel is safely kept in because an inserting hole (12) is blocked by a broken plunger (41).

Effect of Device

This device can prevent a pricking of doctor, nurse and other medical employee because a needle used for a patient is inserted into the inside of a barrel and kept in.

A syringe having a sharp needle should be treated with much care, whether it is used or not. Especially, in case of a blood-stained needle used for a patient, it should be treated most carefully.

The diseases such as hepatitis, AIDS and the like can be transmitted through blood. Therefore, a needle used for such a patient should be handled with utmost care.

This device has an advantage that a needle is safely kept in a barrel because a plunger is broken off after a needle of a syringe is thoroughly inserted into a barrel. A broken-off plunger is inserted into a barrel through an inserting hole. An inserting hole is blocked with a broken plunger so that a needle can be kept in and treated safely.

Thus this is a useful device which makes a used syringe not to be reused and prevents infectious diseases from spreading.

This relates to a device for preventing that disposable syringe is reused and that doctors, nurses, medical employees or others are pricked by the used needle by means of inserting it into a barrel after injection. The needle is attached to the front of a barrel with a needle inserting device, an inserting part is made on male extensions in the front end of the plunger which is inserted into a barrel and a connecting part is made in the back end of a needle inserting device. A male extension of a plunger is assembled with a needle locking device and a needle inserting device which a needle is attached to is inserted into a barrel when a plunger is pulled back. A needle inserting device is kept in the inside of a barrel. Therefore, user doesn't be pricked by the used needle. Consequently, this safety syringe can prevent infectious diseases such as hepatitis and AIDS from spreading.

Some important aspects of the safety syringe according to the second embodiment are as follows:

This safety single use syringe is composed of a barrel (11), a needle (21), a plunger (41) and a needle inserting device (31), same as a general syringe which has a barrel into which the liquid medicine is sucked, a piston and a plunger inside the barrel, and a needle is put on the front tip of the barrel. There s a number of projections (13) in the inside of the front end of an inserting hole (12) of the above barrel (11), the circular stop prominence (15) at the inner surface of a barrel (11), a circular restraining prominence (16) inside the rear end of a barrel, a needle fixing device (32) to insert a needle (21) at the center of a needle inserting device (31), a number of "L" shaped grooves (34) with the wide entrances at an outer surface (33) of a cylindrical part of a needle fixing device (32) in order to be assembled with a projection (13) located at an inner surface of an inserting hole (12) of the above cylindrical barrel (11), an O-ring (35) in the rear of the groves, a number of the inserting grooves (37), a connecting device (43) of upper and lower part with restraining prominences (43') at the front end of a plunger (41) to be assembled with a piston (42), an empty part (47) at the front end of a plunger (41) to be assembled with a piston (42), a cutting notch (45) at the front part of a plunger

(41) in order to be easily broken off, a circular stop prominence (50) at the front part of a plunger (41) reaching to the rear of a piston (42), a rear stop projection (51) at the longitudinal center of a plunger, an empty part longitudinally from a rear stop projection (51) to a cutting notch (45) in the central inside of a plunger.

Figure 11:
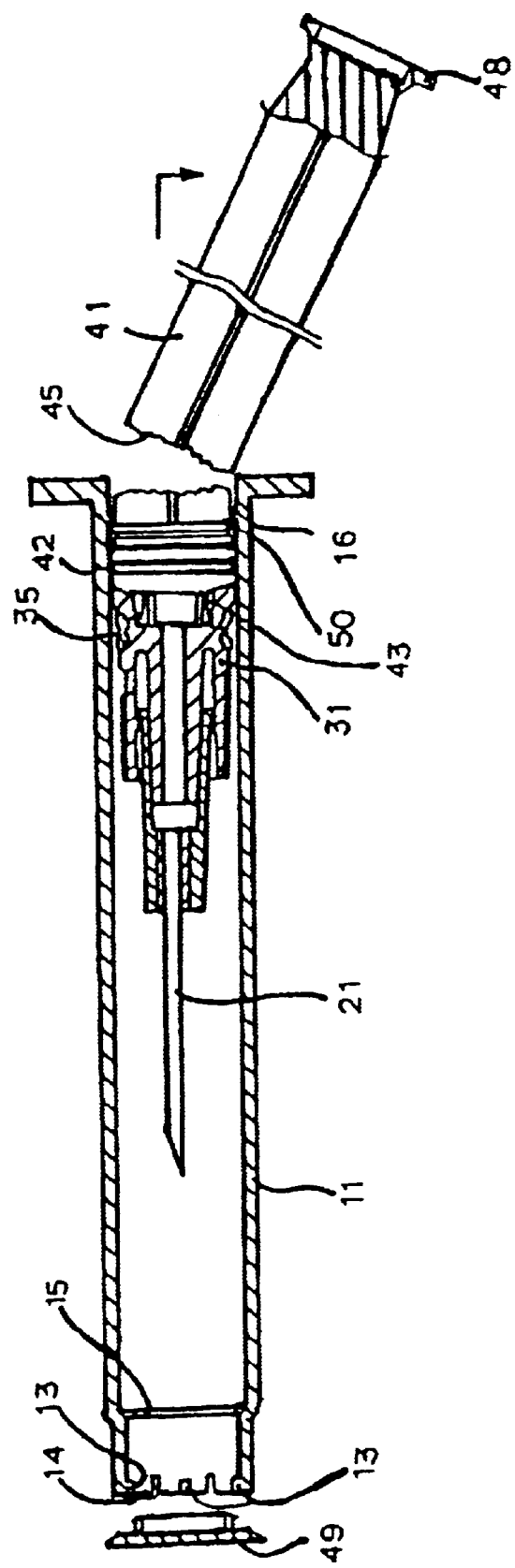
FIG. 11 is a cross-sectional view of this device which shows the breaking of the plunger after pulling the plunger back into the cylinder in order to keep the syringe needle and the syringe needle fixer inside the cylinder.
Figure 12:
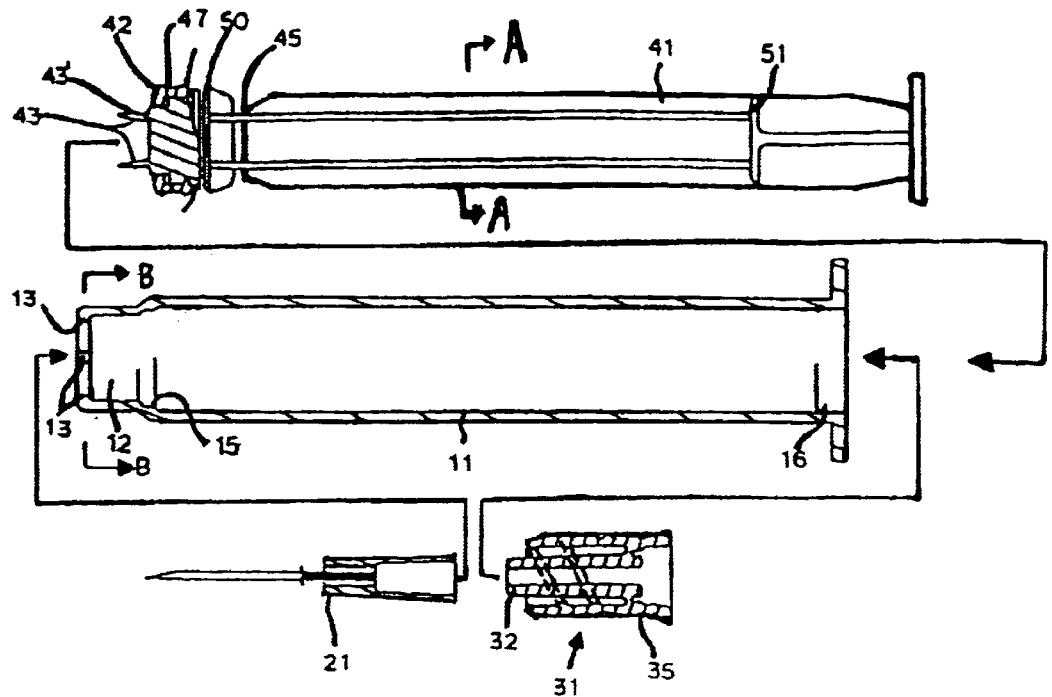
FIG. 12 is a partial longitudinal cross-section of the syringe.
Figure 13:
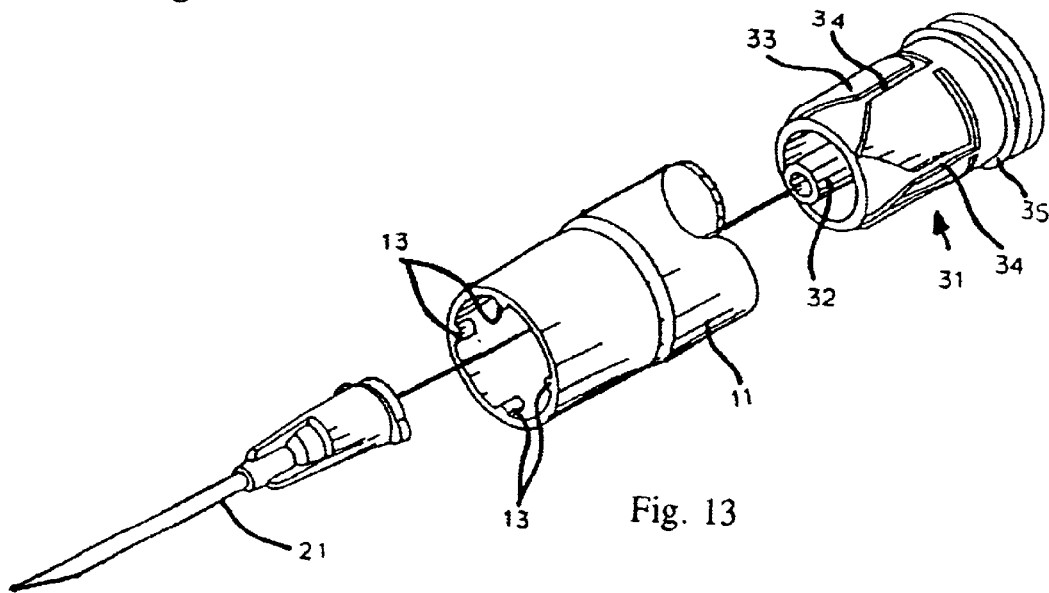
FIG. 13 is an isometric exploded view of a needle inserting device.
Figure 14:
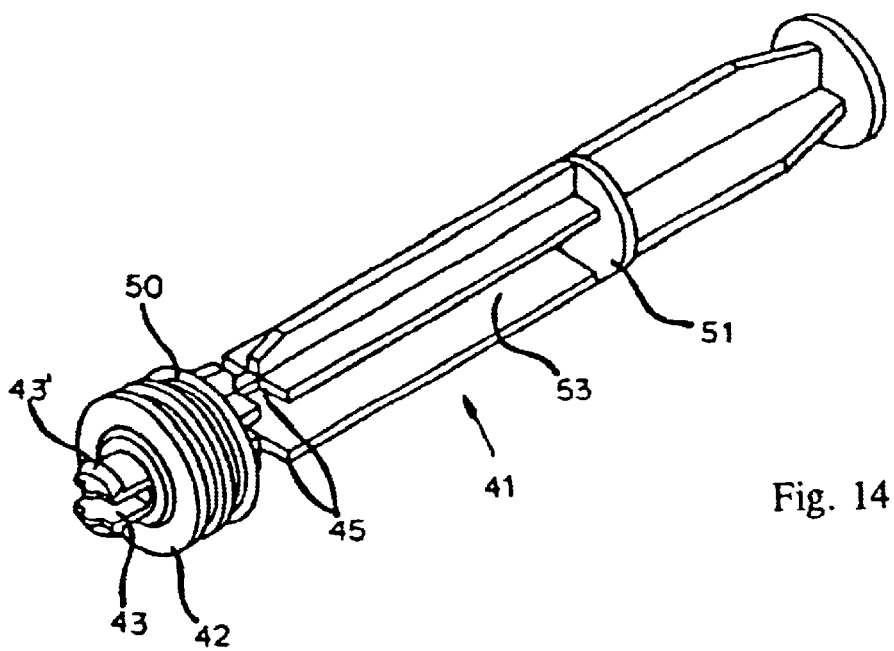
FIG. 14 is a view of the plunger.
Figure 15:
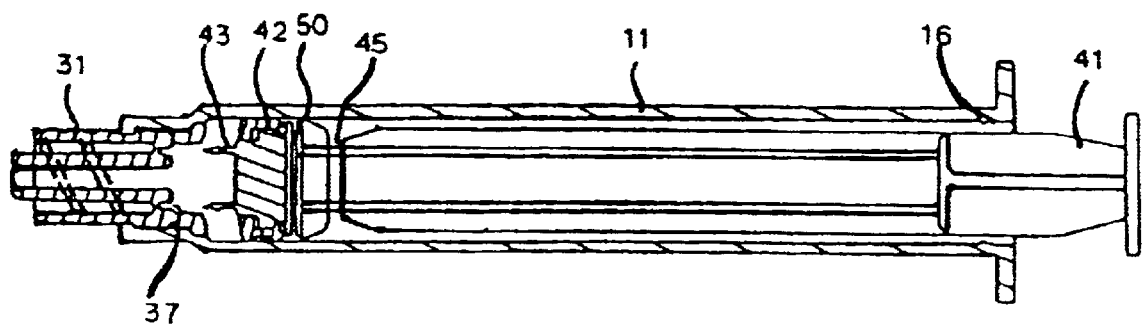
FIG. 15 is a longitudinal cross-section of the syringe without needle.

A relevant difference between the first and the second embodiment is as follows:

According to the first embodiment, the plunger (41) has a cap (49), which serves to close the front hole of the cylinder (11) after injection, i.e. after retraction of the needle (21) into the cylinder (cp. FIGS. 10 and 11).

Figure 16:
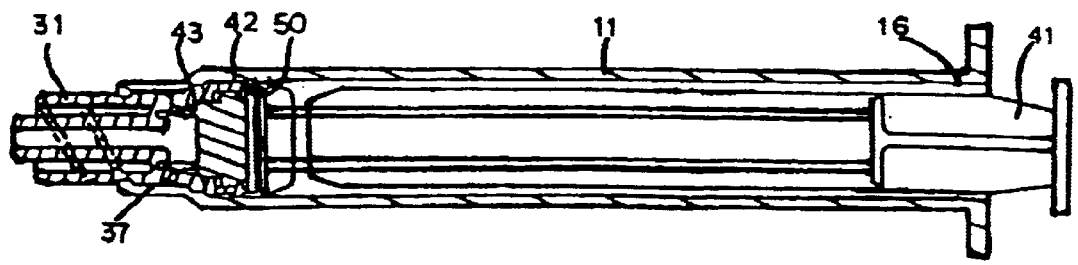
FIG. 16 is a longitudinal cross-section of the syringe without needle that the plunger is assembled with the needle inserting device.
Figure 17:
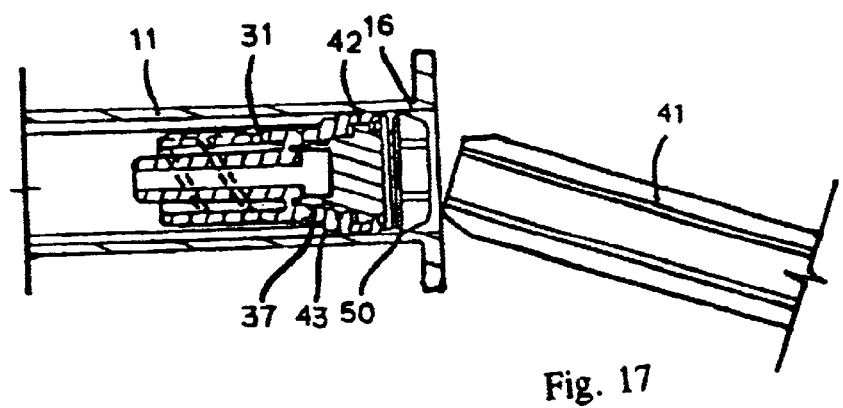
FIG. 17 is a partial cross-section which shows breaking off the plunger after injection.
Figure 18:
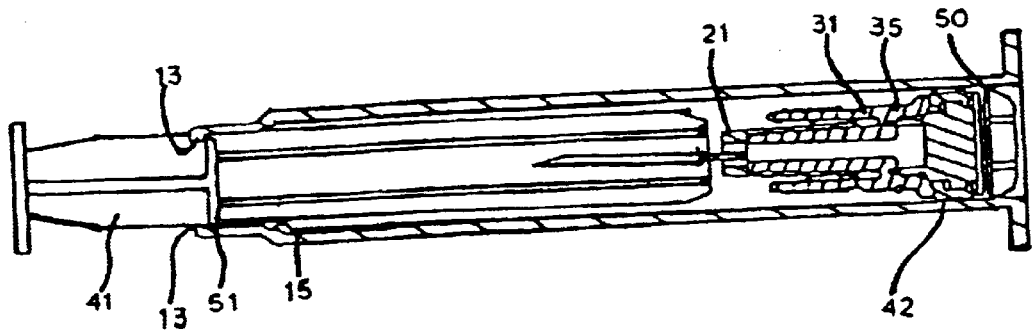
FIG. 18 is a longitudinal cross-section of the syringe covered with a part, separated from the plunger.
Figure 19:
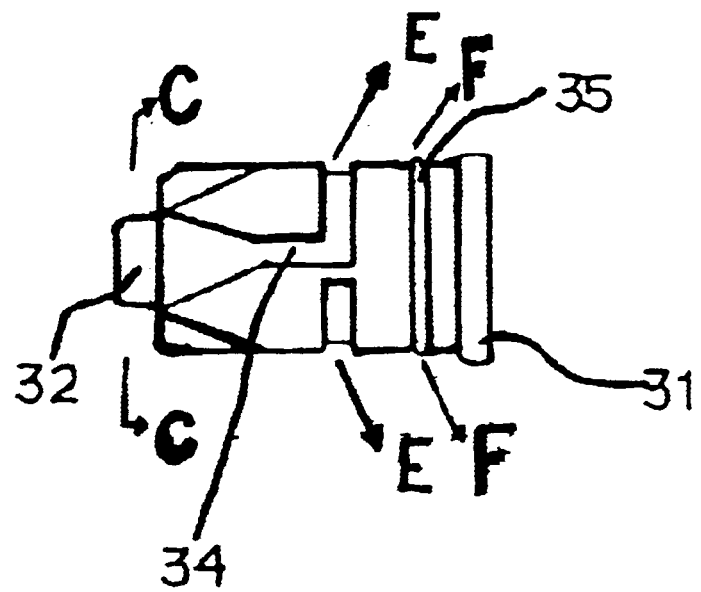
FIG. 19 is a longitudinal view of the needle inserting device.
Figure 20:
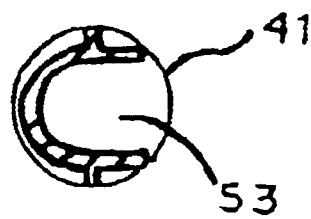
FIG. 20 is an A—A line cross-section in FIG. 12.
Figure 21:
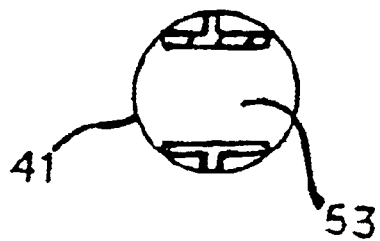
FIG. 21 is another A—A line cross-section in FIG. 12.
Figure 22:
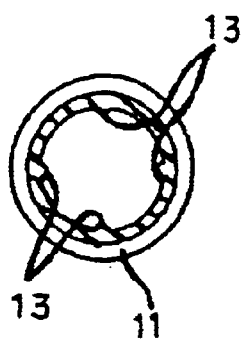
FIG. 22 is a B—B line cross-section in FIG. 12.
Figure 23:
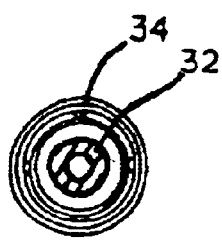
FIG. 23 is a C—C line cross-section in FIG. 19.
Figure 24:
FIG. 24 is an E—E line cross-section in FIG. 19.
Figure 25:
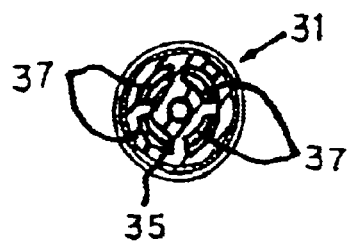
FIG. 25 is an F—F line cross-section in FIG. 19.

According to the second embodiment, a part of the plunger (11) itself serves (after breaking the plunger) to close the front hole of the cylinder (11) after injection, i.e. after retraction of the needle (21) into the cylinder. To close the front hole, the part of the plunger is inserted into the cylinder (cp. FIGS. 16 and 18) Accordingly, the costs for the manufacturing of the cap (e.g. the cost for providing a mold) are saved.

Besides this difference, the general structure and functioning of the first and second embodiment are more or less the same.

In the above specification, the terms barrel and cylinder are used as synonyms. The needle inserting device or needle inserter (31) may as well be termed needle holder.

Third Embodiment

Figure 26:
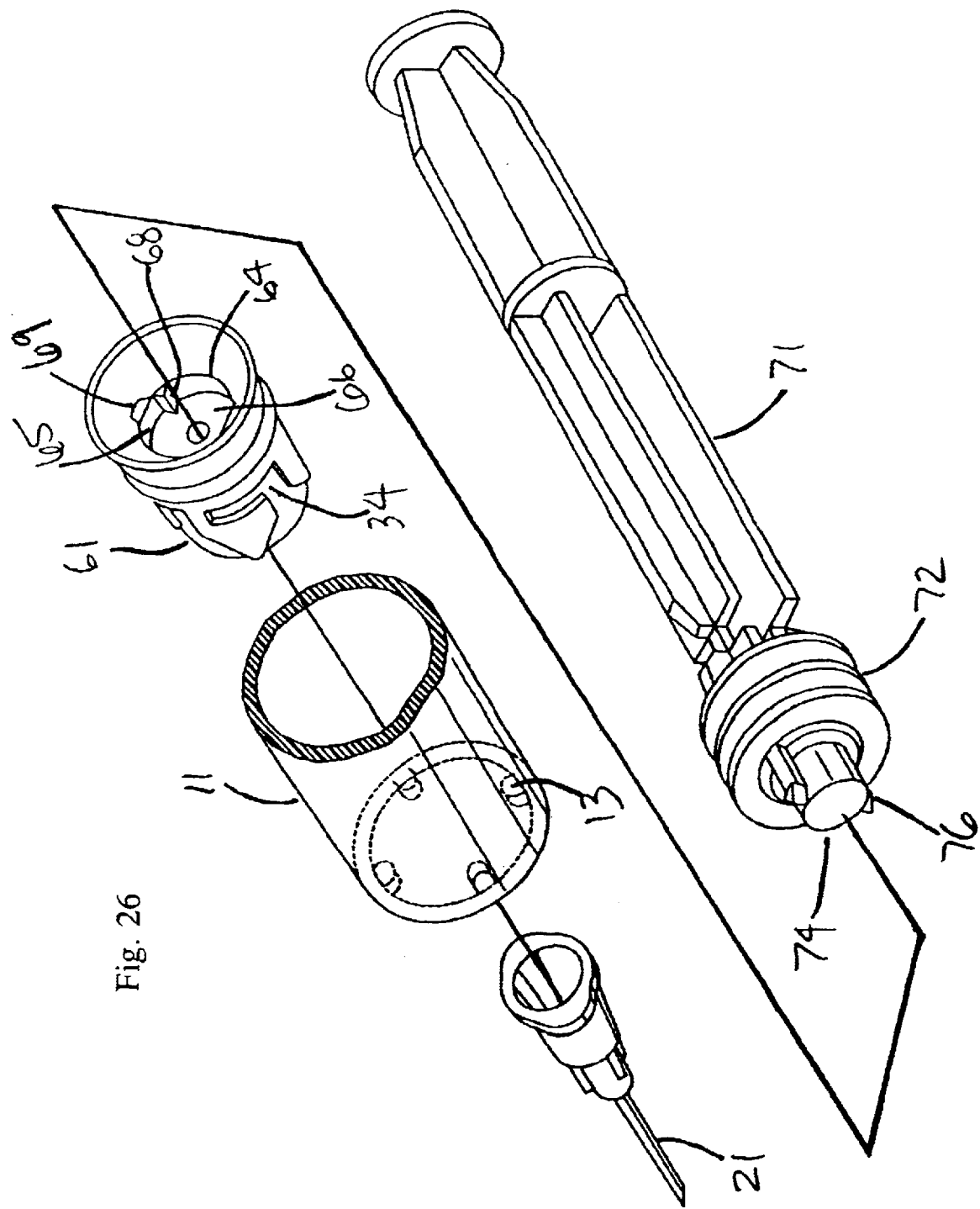
FIG. 26 is a rear perspective view illustrating a needle, portion of a cylinder, and a needle holder, holder and a front perspective view of plunger of a third embodiment all disassembled.

Referring now to FIGS. 26–32, a third embodiment of the present invention may be described. Referring to FIG. 26, shown disassembled are portions of a safety syringe including a hollow needle 21, a thin-walled cylinder or barrel 11 (the forward end being shown), a needle holder 61 and a plunger 71. This embodiment includes an improved connection between the needle holder 61 and plunger 71. Accordingly, the aft portion of the needle holder 61 and forward portion of the plunger 71 are different from the safety syringes described above.

As best shown in FIG. 26, the aft portion of the needle holder 61 includes a generally circular opening 64 leading to a generally cylindrically cavity 66 having an inner surface 65. Around the circular opening 64 are a pair of latching members or tabs 69 which are rounded and project slightly into and aft of the circular opening 65. Inside the cylindrically cavity 66 are a pair of stops or upstanding webs 68 from the inner surface 65. FIGS. 29 and 30 illustrate the aft end of the needle holder 61 in greater detail, including the latching members or tabs 69 and the stops or upstanding webs 68.

Next the corresponding structure in the forward end of the plunger 71 is described. The forward end of the piston 72 includes an anchor member 74 consisting of a pair of flukes 76. The flukes 76 and the anchor member 74 are sized to be received through the circular opening 64 in the aft portion of the needle holder 61 and into the cylindrical cavity 66 in a close clearance or slight interference fit. FIG. 31 illustrates the plunger 71 anchor member 74 inside the needle holder 61 cylindrical cavity 66.

Having described the structure of the third embodiment, now its operation and use is described, in particular the improved coupling of the plunger 71 and needle holder 61. Also referring to FIG. 27, upon dispensing the fluid contained in the cylinder or barrel 11, the forward portion of the plunger 71 or piston 72 is near the needle holder 61. Further pushing the plunger 71 forward causes the anchor member 74 to travel through the circular opening 65 lodge itself inside the cylindrical cavity 66 of the needle holder 61. See FIG. 32. Then rotating the plunger 71 clockwise causes the anchor member 74 flukes 76 to rotate until they contact the stops or upstanding webs 68. At this point the flukes 76 are housed behind the latching members or tabs 69, thereby coupling the plunger 71 and needle holder 61 together. If the plunger 71 and needle holder 61 were somehow inadvertently coupled, merely reversing the above steps, i.e. rotating counterclockwise and pulling the plunger 71 will separate the two.

The typical next step as described above would be continued clockwise rotation of the plunger 71 causing the needle holder 61 to turn as the projections 13 at the forward end of the cylinder or barrel 11 ride inside the L-shaped slots 61 at the forward portion of the needle holder 61. Then it is possible to pull the hollow needle 21 and needle holder 61 aft until the hollow needle 21 is entirely inside the cylinder or barrel 11. Lastly, the plunger 71 sticking out the aft end of the cylinder or barrel may be broken off at a weakened section of the plunger shaft, thereby leaving the hollow needle 21 inside the cylinder or barrel 11 and preventing reuse of the device. A removable cap 49 from the aft end of the plunger 71 may be placed over the forward end of the cylinder or barrel 11.

What is claimed is:

1. A safety syringe for injecting or withdrawing fluids and avoiding inadvertent needle sticks after use comprising:

a thin walled barrel having an inner surface, a forward end and a forward edge, and an aft end, the barrel fillable with the fluids;

a generally cylindrically shaped needle holder having an outer surface, a forward end and an aft end, and a central axis, the needle holder outer surface slidably engaged with the inner surface of the barrel;

a hollow needle attached to the forward end of the needle holder;

the needle holder having a passageway near the central axis from the forward end to the aft end of the needle holder, such that the hollow needle and barrel are in fluid communication;

the outer surface of the needle holder having a plurality of generally L-shaped grooves;

the forward end of the inner surface of the barrel having a plurality of protrusions sized to be received by the plurality of generally L-shaped grooves, to releasably secure the needle holder to the forward end of the barrel;

the aft end of the needle holder having a generally cylindrically shaped cavity having an inner surface with a plurality of upstanding webs;

a plunger having a central axis and having a forward end and an aft end, the plunger at the forward end having a piston having an outer surface slidably engaged with the inner surface of the barrel, the piston having a rod extending to the aft end of the plunger;

the forward end of the plunger further having an anchor member;

the aft end of the needle holder having a generally circular opening sized to receive the anchor member and having a latching member sized to retain the anchor member inside the cavity of the needle holder, the latching member being portions of the opposing of reduced diameter; and the anchor member having a plurality of flukes sized to catch acting as stops inside on the plurality of upstanding webs to enlarge the latching members, the needle holder cavity as the plunger is rotated about the central axis; and the upstanding webs located adjacent the latching members;

the forward end of the piston rod having a reduced cross section;

whereby after use of the safety syringe the plunger anchor may be inserted inside the needle holder cavity and the plunger rotated about the central axis, and the hollow needle pulled inside the barrel and the plunger broken off at the reduced cross section.

2. The safety syringe of claim 1 wherein the plurality of L-shaped slots have widened V-shaped entrances for ease of receiving the plurality of protrusions in assembling the safety syringe.

3. The safety syringe of claim 1 further comprising an O-ring on the outer surface of the needle holder for sealing any gap between the needle holder and the inner surface of the barrel.

4. The safety syringe of claim 1 further comprising at least one O-ring on the outer surface of the piston for sealing any gap between the outer surface of the piston and the inner surface of the barrel.

5. The safety syringe of claim 1 wherein the reduced cross section is a notch in the piston rod.

6. The safety syringe of claim 1 wherein the plurality of protrusions are at the forward edge of the inner surface of the thin walled barrel for ease of manufacture.

7. The safety syringe of claim 1 wherein the barrel has a substantially constant diameter except for the plurality of protrusions.

8. The safety syringe of claim 1 wherein the aft end of the plunger has a cap to facilitate pushing the plunger forward, and at least a portion of the cap is removable to cover the forward end of the barrel upon the needle being retracted into the barrel.

* * * * *